United States Patent [19]

Jordan

[11] 3,991,108

[45] Nov. 9, 1976

[54] CARBOXYLATE FLUORINATION PROCESS

[76] Inventor: Robert Kenneth Jordan, The Carlton House, Suite 1431, 550 Grant St., Pittsburgh, Pa. 15219

[22] Filed: Oct. 31, 1973

[21] Appl. No.: 411,487

[52] U.S. Cl. .............................. 260/544 F; 260/408; 260/453 P; 260/500.5 R; 423/551; 423/554; 423/558; 423/302; 423/365; 423/483
[51] Int. Cl.$^2$................. C07C 51/58; C07C 118/00
[58] Field of Search......... 260/544 F, 544 K, 544 M, 260/408, 453 P; 423/302, 365, 483

[56] References Cited
UNITED STATES PATENTS 2,791,608   5/1957   Golding .............................. 260/544

FOREIGN PATENTS OR APPLICATIONS 146,690   10/1902   Germany ........................... 260/544

OTHER PUBLICATIONS

March, "Advanced Organic Chemistry," McGraw-Hill (1968) N.Y., p. 335.
Fischer et al., C.A. 60 13917c (1964).
Szabo et al., C.A. 55 13013f (1961).
Vogel, "Practical Organic Chemistry," Wiley & Sons Inc., N.Y. (1962), pp. 122–125.
Jonas, C.A. 54 P 3891g.
Linhard et al., C.A. 34 40058 (1940).
Traube et al., Berichte 52B 1272 (1919).
Traube et al., Berichte 52B 1293 (1919).

*Primary Examiner*—Norman Morgenstern

[57] ABSTRACT

A process for the fluorination of carboxylate compounds to the corresponding acyl fluoride or carbamoyl fluoride, the latter compounds decompose to isocyanates and hydrogen fluoride, wherein the carboxylic acid, its anhydride or metal salt is intimately mixed with a metal fluorosulfonate and heated at a temperature at which the gaseous carboxylic acid fluoride is formed or decomposed.

11 Claims, No Drawings

CARBOXYLATE FLUORINATION PROCESS

This invention relates to a process for the production of acyl fluorides or hydrogen fluoride and cyanic acid or isocyanates.

Acyl fluorides are fluorinating agents, a source of hydrogen fluoride and intermediates for the production of fluorocarbons. They are usually made by the reaction of hydrogen fluoride or a metal fluoride with the corresponding acyl chloride. But aside from phosgene, made by the direct chlorination of carbon monoxide, the carboxylic acid chlorides are not simply synthesized. Although carbonyl fluoride can be directly produced from elemental fluorine and carbon monoxide, elemental fluorine is prohibitively expensive. Both sulfur tetrafluoride and sulfonyl fluoride will directly convert carboxylic acids to the corresponding carbonyl fluoride, but again, these intermediates are too costly.

Isocyanates are valuable intermediates for the production of polyurethane foams and for carbamate insecticides. They are almost universally manufactured by the phosgenation of the corresponding amine, for example;

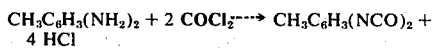

Toluene diisocyanate, above, is used mainly in the making of flexible polyurethane foams. Polymethylene polyphenyleneisocyanate, the phosgenation product of mineral acid catalyzed aniline-formaldehyde condensates, is the preferred isocyanate intermediate for rigid polyurethane foams. Methyl isocyanate can be used for the production of the alphanaphthyl ester of methyl carbamate. But in the commercial production of these isocyanates, hydrogen chloride is an unwanted by-product because it isn't easily liquified and must be transported in the form of a some 30 percent aqueous solution. In most new isocyanate facilities the hydrogen chloride is taken up in water and electrolyzed to chlorine and hydrogen. Several other problems or cost factors exist in the manufacture of isocyanates including the toxicity of phosgene and expensive carbon monoxide which is usually isolated cryogenically from reformed natural gas.

Cyanic acid, often referred to as isocyanic acid, normally exists in the form of a trimer, for example melamine. But at high temperatures it does exist as a monomer and has been proposed as an intermediate for aliphatic isocyanates through its catalyzed addition to olefins. At present there is no inexpensive method for producing the anhydrous product.

Hydrogen fluoride is mainly used as an intermediate to fluorocarbons which enjoy extensive markets through their use as propellants in aerosol cans. Hydrogen fluoride is made commercially by the digestion of fluorspar in sulfuric acid, and, as in the manufacture of phosphoric acid, the fluoride and gypsum by-products represent difficult disposal problems.

Therefore, it is an object of my invention to provide a new and improved process for the production of acyl fluorides.

It is another object to provide a new and improved process for the simultaneous production of carbon monoxide and carbonyl fluoride.

It is a further object to provide a new and improved process for the simultaneous production of cyanic acid and hydrogen fluoride.

It is yet another object to provide a new and improved process for the simultaneous production of isocyanates and hydrogen fluoride.

It is still another object to provide a new and improved process for the separation of benzene carboxylic acid mixtures My invention is a process for, and certain compositions of, the production of acyl and carbamoyl fluorides, and decomposition products thereof, wherein a carboxylic acid, or its anhydride or metal salt, selected from at least one of hydrogen, alkyl, alkenyl, aryl, amino, alkylamino, arylamino, alkylamido, arylamido, phosphamido and sulfamido mono, di and poly carboxylic acids and a fluorosulfonate or fluorosulfinite of a metal fluoride selected from at least one of mono, bi and tri valent metals with a ratio of from about 0.2 to about 3 moles sulfur oxide per equivalent fluoride ion and a ratio of from about 0.2 to about 6 fluoride ion equivalents per equivalent carboxylate is heated at a temperature in the range of from about −20°C to about 600°C.

I have found that the heating of an intimate mixture of powders of equimolar quantities of calcium oxalate with calcium fluorosulfonate to about 130°C results in the evolution of a mixture of carbonyl fluoride and carbon monoxide. There is no trace of oxalyl fluoride. The same products are obtained when the calcium oxalate is replaced by an oxalate of another alkaline earth metal, or, by any of the mono, bi or tri valent metals. The unique result was unaltered by other changes. But when a mole of calcium formate and a mole of calcium fluorosulfonate were mixed and heated to about 120° to 130° C it was found that the product composition was variable. On slow heating, only hydrogen fluoride and carbon monoxide was found, but on rapid heating on a thin sheet of metal, formyl fluoride was detected in roughly 25 percent yield. As formyl fluoride is unstable at above 50°C, the result is mildly surprising. Other metal formates, whether mono, bi or tri valent metals, gave about the same results. The various metal salts of acetic acid under the same conditions yield acetyl fluoride in good yields. Metal salts of other aliphatic acids interact with calcium fluorosulfonate beginning at between 100° and 170° C to give the corresponding acyl fluoride, usually in high yields. The process appears to follow the general equation;

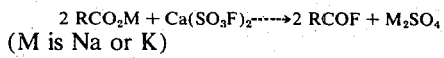

(M is Na or K)

Other aliphatic acid salts include isobutyric acid, cyclohexane carboxylic acid, methacrylic acid, maleic acid and saponified acid mixtures from natural fats and oils.

The metal salts of aromatic carboxylic acids also participate smoothly in the process of my invention. When two moles of potassium benzoate and one mole of calcium fluorosulfonate are heated rapidly to over 180°C, gaseous benzoyl fluoride is evolved. On analysis the product analyzes at about 98 percent purity. The salts of the three phthalic acid isomers with calcium fluorosulfonate yield the corresponding phthaloyl, isophthaloyl and terephthaloyl fluorides, but as these boil at over 200°C operation at reduced pressure may optionally be employed. Although a mixture of the isomers may be fractionally distilled for separation, it is interesting to note that the melting point of terephthaloyl fluoride is 122°C while both phthaloyl and isophthaloyl fluorides melt at about 40° C. Thus fractional crystallization readily separates the para isomer while the ortho and meta isomers have a boiling point difference of about 30° C. The three isomers of benzene tri(carbonyl fluorides) all boil at above 250° C at atmospheric pressure and have been prepared by the process. The acyl fluorides of hemimellitic, trimellitic and trimesic acids have not been reported in the literature. By very rapid heating the benzene tetra(carbonyl fluorides) can also be made at atmospheric pressure by the process of my invention, but they are ideally produced at about 200° C at from 10 to 50 mm Hg pressure where reasonable yields can be obtained. At higher temperatures the benzene tetra(carbonyl fluorides) have a tendency to decarbonylate as evidenced by the presence of fluorine atoms in the benzene ring. The fact that small quantities of benzene penta(carbonyl fluoride) and benzene hexa(carbonyl fluoride) were obtained overhead by the treatment of the salts obtained by the alkaline air oxidation of coal with calcium fluorosulfonate and rapid heating at reduced pressure, is an indication of the unusual nature of these acyl fluorides.

In a separate application I have disclosed a process for the preparation of N-substituted carbamic acid metal salts. This was the result of discovering that sodium carbamate and calcium fluorosulfonate react under conditions identical those noted above to produce either carbamoyl fluoride or a mixture of cyanic acid and hydrogen fluoride. In reality, even with rapid heating the yields of carbamoyl fluoride are not particularly high, but the product is easily prepared and separated. With slow heating and higher temperatures, cyanic acid formation is favored and it is easily trapped out cold as a liquid. As it is unstable at above 0° C it must be stored cold. Cyanic acid is a valuable intermediate to cyamelide, cyanuric acid, melamine and isocyanates. The calcium salt of N-methyl carbamic acid and an equimolar amount of calcium fluorosulfonate begin to react at about 140° C and again, the nature of the products can be varied with the rate of heating. Methyl carbamoyl fluoride can be obtained in fair yields be rapid heating, but the process is more ideal for the production of its thermal decomposition products, namely methyl isocyanate and hydrogen fluoride. It appears that the amino group of the carbamic acid salts has no effect on the nature of the process, that a carbamoyl fluoride is probably formed and then thermally and perhaps catalytically decomposed. On heating the calcium salt of the dicarbamic acid of hexamethylene diamine with calcium fluorosulfonate, excellent yields of hexamethylene diisocyanate and hydrogen fluoride are obtained. Similarly, aromatic carbamic acid salts behave under conditions akin to those used for the aromatic carboxylic acid salts, yielding a mixture of hydrogen fluoride and the corresponding isocyanate. Thus the 80:20 mixture of 2,4- and 2,6- toluene diamines can be converted to the corresponding mixed toluene dicarbamic acid salts, which when heated with an equivalent quantity of a metal fluorosulfonate at between 150° and 200° C at reduced pressures gives high yields of the toluene diisocyanates and hydrogen fluoride. Phenyl isocyanate and hydrogen fluoride is best made from a metal carbanilate and a metal fluorosulfonate at above 175° C at atmospheric pressure. The acid condensation of aniline with formaldehyde yields 4,4'-methylenedianiline and methylene phenylene amino compounds that can be converted to the corresponding carbamic acid salts. While 4,4'-diphenylmethane diisocyanate can be made from the corresponding salt with a metal fluorosulfonate at reduced pressures in good yields, the higher condensate carbamate metal salts come over in lower yields.

Although difficult to make, the dicarbamic acid metal salts of adipamide and isophthalamide were prepared by transacylation. The products were mixed with calcium fluorosulfonate and heated at reduced pressures to about 200°C where the corresponding acyl isocyanates were found in the condensates.

Several carbamate metal salts were made of sulfuryl amide, phosphorous triamide and phosphoryl triamide; all were mixed with an equivalent amount of a metal fluorosulfonate and heated at reduced pressure to between 180° and 300° C to yield the corresponding sulfonyl diisocyanate, phosphorous triisocyanate and phosphoryl triisocyanate in fair to good yields.

Numerous metal salts of carboxylic acid and carbamic acid compounds were tried to determine the scope of the process. All the mono, bi and tri valent metal salts tested yielded product. These included carboxylates of lithium, sodium, potassium, beryllium, magnesium, calcium, silver, copper, cadmium, zinc, chromium, manganese, iron, nickel and lead. The bi and trivalent salts of manganese, iron and chromium gave about the same results. It is important that the salts be well dried as the fluorosulfonates are highly moisture sensitive.

By a minor variation in the process, acids and anhydrides can be utilized directly in the process. A mole of acetic acid and a mole of calcium fluoride fluorosulfonate, also known as calcium monofluorosulfonate, $CaF(SO_3F)$, yields a mixture of hydrogen fluoride and acetyl fluoride starting at a temperature of about 40° C; as in the equation;

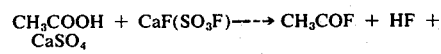

$$CH_3COOH + CaF(SO_3F) \longrightarrow CH_3COF + HF + CaSO_4$$

Uniquely, oxalic gives carbonyl fluoride and carbon monoxide along with hydrogen fluoride, but the carbonyl fluoride yield is lower than that obtained with the salts of oxalic acid. In most cases the yields were comparable. It is interesting that when an organic carboxylic acid reaches its melting point, the reaction proceeds rapidly. For example, benzoic acid melts at about 120° C and at near that the kinetics are rapid in the exothermic system. Similarly, anhydrides of carboxylic acids interact with calcium fluoride fluorosulfonate to yield the corresponding acyl fluorides. Generally the stoichiometry is expressed by the general equation;

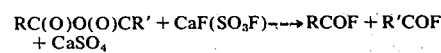

$$RC(O)O(O)CR' + CaF(SO_3F) \longrightarrow RCOF + R'COF + CaSO_4$$

The anhydrides are also inclined to react at about their melting points, but even those with very high melting points usually begin to react at about 150° to 200° C. The acids and anydrides tested in the process included acetic acid, formic acid, acetic formic anhydride, maleic anhydride, cyclohexane carboxylic acid, benzoic acid, benzoic anhydride and phthalic anhydride. The fluorosulfonates used in this part of the work included sulfur trioxide adducts to calcium fluoride, magnesium fluoride, ferrous fluoride and ferric fluoride. Both the mono and di adducts were made of ferric fluoride and tested. A novel variation was discovered when the anhydrides were mixed with a mixture of potassium fluorosulfonate and potassium fluoride and heated. The fluoride ion of potassium fluoride was extracted, ending up in the acyl fluoride. The results can be expressed by the equation;

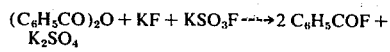

Although not as well, the phenomena is noted even when a mixture of potassium fluoride and calcium fluorosulfonate is used.

Acetic anhydride and benzoic anhydride form adducts with sulfur trioxide. An adduct of the latter containing a mole of sulfur trioxide and a mole of benzoic anhydride in ethylene dichloride was carefully treated with a mole of the calcium salt of N-methyl carbamic acid and then the product was heated with calcium monofluorosulfonate. As methyl isocyanate and benzoyl fluoride were found in the mixture with hydrogen fluoride, it is presumed that the benzoic methyl carbamic anhydride was formed and accounted for the result.

Several experiments were also conducted using phosphoric acid, phosphorus pentoxide, phosphorous trioxide and boron oxide with mixtures of alkali fluorides and fluorosulfonates of sodium, potassium, calcium, magnesium and iron II. Lithium and sodium fluoride give up very little of its fluoride ion, while the other three alkali metal fluorides are ready donors. The products included phosphoryl fluoride, phosphorous trifluoride and boron trifluoride.

Fluorosulfonates can be made in a variety of ways. In the laboratory a simple method is the addition of oleum to a slurry of the metal fluoride in dichloroethane. But on a large scale basis, the direct addition of sulfur trioxide under pressure to the metal fluoride at elevated temperatures is the preferred route. Thus it is possible to obtain a wide range of mixtures. For example, with calcium fluoride the first product obtained is a mixture of calcium fluoride monofluorosulfonate, $CaF(SO_3F)$, in unreacted fluorspar. Then as the addition of sulfur trioxide continues a mixture containing calcium fluorosulfonate, $Ca(SO_3F)_2$, Calcium fluoride fluorosulfonate and unreacted calcium fluoride. Finally, complete addition yields calcium fluorosulfonate. It is surprising that relatively low grade fluorspar can be utilized efficiently to produce the calcium fluorosulfonates. The alkali metal, other alkaline earth metal, zinc, manganous, manganic, ferrous and ferric fluorosulfonates were made and metal fluoride fluorosulfonates were made of the alkaline earth metal, zinc, manganous, ferrous and ferric fluorides. The adduct of two moles sulfur trioxide to one mole of ferric fluoride, $FeF(SO_3F)_2$ was also made and tested. However, as the mineral fluorspar is widely available, its two fluorosulfonates were mostly used in the study. Several metal fluorosulfinites are known. In fact, sulfur dioxide adds directly to potassium fluoride to produce the fluorosulfinite, $KSO_2F$, which, although less stable than the corresponding fluorosulfonate, can participate in the process of my invention. Thus an equimolar mixture of potassium acetate and potassium fluorosulfinite heated to about 120° begins to evolve acetyl fluoride. Examination of the resulting metal salt reveals the presence of potassium sulfite, $K_2SO_3$. At higher temperatures potassium fluorosulfinite disproportionates to potassium fluorosulfonate and sulfur.

The nature of the process is such that it can be varied in many ways. An example is the addition of sulfur trioxide to an intimate mixture of powders of the metal fluoride and metal carboxylate. This imposes the necessity to operate at near or above atmospheric pressure and to remove sulfur trioxide from the products. Another obvious difficulty is possible sulfonation of the carboxylate.

Solvents, or rather liquid media, can also be utilized, ethylene dichloride and dichlorobenzenes are examples, but both yields and kinetics suffer in the use of a liquid media.

The particle sizes of the intermediates should be preferrably less than 100 mesh as yields decrease above that size. However, it is possible to conduct grinding in the operation of the process. For example, by the addition of steel grinding balls to promote mixing, heat transfer and of course grinding. The mixtures made at low temperature where no reaction takes place, can be pelletized without a binder. But a polyacrylate binder can be used and a thin outer coating of paraffin is desirable to moisture degradation.

The utility of my process in the production of isocyanates is obvious, as a valuable coproduct, hydrogen fluoride, accompanies the product. Further, there are no solvent and tar problems. The production of acyl fluorides is especially advantageous in the separation of mixtures of acids or their derivatives. An outstanding example comes from study with the salts of acids produced in the alkaline air oxidation of coal averaging about 4 carboxylate groups per benzene ring. Most of products can be recovered over-head and separated by fractionation. Moreover, the salts can be partially decarboxylated and optionally isomerized by known processes to produce mixtures containing mainly dicarboxylates of benzene and especially the salts of terephthalic acid. As noted earlier, the process of my invention is ideal for the separation and purification of the components, and again, yields hydrogen fluoride as a coproduct in the addition of water to form the acid, or alcohol to produce the ester.

According to the provision of the patent statutes, I have explained the principle of my invention and have illustrated and described what I now consider to represent its best embodiment. However, I desire to have it understood that within the scope of the appended claims, the invention may be practiced otherwise than as specifically illustrated and described.

I claim:

1. A process for the production of acyl fluorides and carbamoyl fluorides and their corresponding isocyanates which comprises reacting a carboxylic acid, or anhydride or metal salt thereof, selected from the group consisting of formic acid or an alkyl, alkenyl, aryl, carbamic, alkylamino, arylamino, alkylamido, arylamido, phosphamido and sulfamido mono, di- or poly-carboxylic acid, with a sulfur oxide adduct of a metal fluoride selected from the group consisting of sulfur trioxide adducts of mono-. bi- and tri-valent metal fluorides and sulfur dioxide adducts of monovalent metal fluorides in a ratio of from about 0.2 to about 3 moles of sulfur oxide per equivalent of metal fluoride, and from about 0.2 to about 6 moles of sulfur oxide adduct per equivalent of carboxylic acid feed at a temperature in the range of from about −20°to about 600°C.

2. The process of claim 1 where the carboxylic acid is selected from the group consisting of formic, oxalic, fatty and benzene mono-, di- and poly- carboxylic acids and is reacted with the sulfur oxide adduct at a temperature in the range of from about 0° to about 500° C.

3. The process of claim 1 where the anhydride is selected from the group consisting of carbonic, formic, oxalic, fatty, benzene and naphthalene mono-, di- and poly-carboxylic acid anhydrides and is reacted with the sulfur oxide adduct at a temperature in the range of from about 0° C to about 500° C at a pressure of the range of from about 1 mm Hg to about 100 atmospheres.

4. The process of claim 1 where the metal salt of the carboxylic acid is selected from the group consisting of the mono-, bi- and tri-valent metal salts of formic, fatty, benzene and naphthalene mono-, di- and poly-carboxylic acids and is reacted with the sulfur oxide adduct at a temperature in the range of from about 0° to about 500°C at a pressure in the range of from about 1 mm Hg to about 100 atmospheres.

5. The process of claim 4 where the metal carboxylate is an alkali or alkaline earth metal salt of a mixture comprising benzene dicarboxylic acids.

6. The process of claim 1 where the metal salt of the carboxylic acid is selected from the group consisting of mono-, bi- and tri-valent metal salts of carbamic and N-organo-substituted carbamic acids of fatty amines, hexamethylene diamine, aniline, toluene diamines and aniline-formaldehyde condensates and is reacted with the sulfur oxide adduct at a temperature in the range of from about 50° C to about 500° C at a pressure in the range of from 1 mm Hg to about 100 atmospheres.

7. The process of claim 1 where the metal salt is selected from the group consisting of the mono-, bi- and tri-valent metal carbamate substituted sulfuryl amide, phosphorous triamide or phosphoryl triamide.

8. The process of claim 1 where the metal salt of the carboxylic acid is selected from the group consisting of the mono-, bi- and tri-valent metal salts of aminoformic acid substituted alkyl, alkylene, aryl, or arylene mono- or di-amides.

9. The process of claim 5 wherein the product mixture comprising terephthaloyl fluoride and at least one one phthaloyl and isophthaloyl fluorides is cooled in the range of from about −20° to about 120° C to fractionally crystallize terephthaloyl fluoride.

10. A process for the simultaneous production of carbonyl fluoride and carbon monoxide wherein a metal oxalate selected from the group consisting of mono-, bi and tri-valent metal oxalates is reacted with a sulfur oxide adduct of a metal fluoride selected from the group consisting of sulfur trioxide adducts of mono-, bi- and tri-valent metal fluorides and sulfur dioxide adducts of mono-valent metal fluorides in a ratio of from about 0.2 to about 3 moles sulfur oxide per equivalent on metal fluoride, and from about 0.2 to about 6 moles sulfur oxide adduct per equivalent of metal oxalate at a temperature in the range of from about 0°C to about 600° C.

11. The process of claim 10 where the metal oxalate is insoluble in water and reacted with the sulfur oxide adduct at a temperature in the range of from about 500° to about 500° C.

* * * * *

UNITED STATES PATENT OFFICE
CERTIFICATE OF CORRECTION

Patent No. 3,991,108          Dated Nov. 9, 1976

Inventor(s) Robert Kenneth Jordan

It is certified that error appears in the above-identified patent and that said Letters Patent are hereby corrected as shown below:

In column 8 claim 11, last line reading " $500°$ to " should read " $50°$ to "

Signed and Sealed this

*Twenty-fourth* Day of *July 1979*

[SEAL]

*Attest:*

LUTRELLE F. PARKER

*Attesting Officer*      *Acting Commissioner of Patents and Trademarks*